United States Patent
Masuoka et al.

(10) Patent No.: US 9,439,933 B2
(45) Date of Patent: Sep. 13, 2016

(54) SKIN PROPERTIES IMPROVING AGENT FOR ORAL ADMINISTRATION

(75) Inventors: Norie Masuoka, Minato-ku (JP); Mitsuyoshi Kano, Minato-ku (JP); Kouji Miyazaki, Minato-ku (JP); Toshiro Sone, Minato-ku (JP)

(73) Assignee: KABUSHIKI KAISHA YAKULT HONSHA, Tokyo (JP)

( * ) Notice: Subject to any disclaimer, the term of this patent is extended or adjusted under 35 U.S.C. 154(b) by 0 days.

(21) Appl. No.: 13/805,908

(22) PCT Filed: Jun. 27, 2011

(86) PCT No.: PCT/JP2011/064681
§ 371 (c)(1),
(2), (4) Date: Dec. 20, 2012

(87) PCT Pub. No.: WO2012/002322
PCT Pub. Date: Jan. 5, 2012

(65) Prior Publication Data
US 2013/0095073 A1   Apr. 18, 2013

(30) Foreign Application Priority Data
Jun. 28, 2010   (JP) ................. 2010-145766

(51) Int. Cl.
| | | |
|---|---|---|
| A61K 35/745 | (2015.01) | |
| A61K 35/74 | (2015.01) | |
| A23L 1/30 | (2006.01) | |
| A61K 31/702 | (2006.01) | |
| A61K 35/20 | (2006.01) | |
| A61K 35/744 | (2015.01) | |

(52) U.S. Cl.
CPC .............. *A61K 35/74* (2013.01); *A23L 1/3014* (2013.01); *A61K 31/702* (2013.01); *A61K 35/20* (2013.01); *A61K 35/744* (2013.01); *A61K 35/745* (2013.01); *A23V 2002/00* (2013.01)

(58) Field of Classification Search
CPC ........... A61K 2300/00; A61K 35/745; A61K 35/741; A23V 2200/318; A23V 2200/3204
USPC ........................................ 424/93.3
See application file for complete search history.

(56) References Cited

U.S. PATENT DOCUMENTS

| | | | |
|---|---|---|---|
| 5,895,648 A | 4/1999 | Cavaliere Vesely et al. | |
| 2003/0133921 A1 | 7/2003 | Ohishi et al. | |
| 2005/0031735 A1 | 2/2005 | Serata et al. | |
| 2005/0069505 A1* | 3/2005 | Breton et al. | 424/59 |
| 2005/0106131 A1 | 5/2005 | Breton et al. | |
| 2006/0008453 A1* | 1/2006 | Breton et al. | 424/93.45 |
| 2007/0122454 A1 | 5/2007 | Yoshimura et al. | |
| 2010/0151039 A1 | 6/2010 | Yoshimura et al. | |
| 2010/0291049 A1 | 11/2010 | Izawa et al. | |
| 2011/0182934 A1* | 7/2011 | Potappel-van 'T Land et al. | 424/203.1 |

FOREIGN PATENT DOCUMENTS

| | | |
|---|---|---|
| JP | 7 265064 | 10/1995 |
| JP | 10 286078 | 10/1998 |
| JP | 2001 252048 | 9/2001 |
| JP | 2005 206578 | 8/2005 |
| JP | 2005 525348 | 8/2005 |
| JP | 2007 39423 | 2/2007 |
| JP | 2009 114080 | 5/2009 |
| JP | 2010 6757 | 1/2010 |
| WO | 03 040350 | 5/2003 |
| WO | 2005 018653 | 3/2005 |
| WO | 2008 026318 | 3/2008 |
| WO | 2009 151331 | 12/2009 |

OTHER PUBLICATIONS

Kano et al., Consecutive intake of fermented milk containing Bifidobacterium breve strain Yakult and galacto-oligosaccharides benefits skin condition in healthy adult women. Bioscience of Microbiota, Food and Health, vol. 32, No. 1 (2013) pp. 33-39.*

Sugimoto et al., Photoprotective effects of Bifido bacterium breve supplementation against skin damage induced by ultraviolet irradiation in hairless irless mice. Photodermatology, Photoimmunology & Photomedicine, vol. 28 (2012) pp. 312-319.*

Rass et al., UV damage and DNA repair in malignant melanoma and nonmelanoma skin cancer.Advanced Experimental Medical Biology, vol. 624 (2008) pp. 162-178.*

International Search Report Issued Aug. 2, 2011 in PCT/JP11/64681 Filed Jun. 27, 2011.

Extended European Search Report issued Dec. 13, 2013 in Patent Application No. 11800786.3.

Sandrine Menard, et al., "Stimulation of Immunity Without Alteration of Oral Tolerance in Mice Fed with Heat-Treated Fermented Infant Formula", Journal of Pediatric Gastroenterology and Nutrition, vol. 43, Jan. 1, 2006, pp. 451-458.

* cited by examiner

*Primary Examiner* — Kara Johnson
(74) *Attorney, Agent, or Firm* — Oblon, McClelland, Maier & Neustadt, L.L.P (57) ABSTRACT

Disclosed is a skin property-improving agent which exerts excellent effects by oral administration. The skin property-improving agent for oral administration contains, as an active ingredient, a bacterium belonging to the genus *Streptococcus* and a bacterium belonging to the genus *Bifidobacterium*, or fermented milk containing the two bacteria.

13 Claims, 9 Drawing Sheets

SKIN PROPERTIES IMPROVING AGENT FOR ORAL ADMINISTRATION

This application is a National Stage of PCT/JP11/064681 filed Jun. 27, 2011 and claims the benefit of JP 2010-145766 filed Jun. 28, 2010.

TECHNICAL FIELD

The present invention relates to a skin property-improving agent which improves skin properties such as the water content of the stratum corneum by oral ingestion.

BACKGROUND ART

Exposure of the skin to ultraviolet rays causes inflammation, immune suppression, oxidation, DNA damage, and the like, resulting in reduced moisture content, wrinkle formation, reduced elasticity, acceleration of aging of the skin, and the like. In general, for the aforementioned aggravated skin properties, moisturizing agents and other ingredients are administered in the form of an external preparation.

Meanwhile, a means for the improvement of skin properties by orally ingesting moisturizing ingredients, anti-inflammatory ingredients, and the like has recently been reported (Patent Documents 1 and 2). Further, it has been reported that *Streptococcus thermophilus* inhibits atopic dermatitis (Patent Document 3) and that bacteria belonging to the genus *Bifidobacterium* improve the skin thickness and a reduction in elasticity (Patent Docuement 4), respectively.

RELATED ART DOCUMENT

Patent Document

[Patent Document 1] JP-A-2001-252048
[Patent Document 2] JP-A-2005-206578
[Patent Document 3] JP-A-2007-39423
[Patent Document 4] JP-A-2010-6757

SUMMARY OF THE INVENTION

Problem to be Solved by the Invention

However, conventional skin property-improving agents for oral administration do not have sufficient effects, and therefore, materials having better skin property-improving effects have been demanded.

Accordingly, an object of the present invention is to provide a skin property-improving agent which exerts excellent effects by oral ingestion.

Means for Solving the Problem

In light of the above, the present inventors have studied the effect of oral administration of a variety of lactic acid bacteria groups and fermented milk prepared using the bacteria on the skin troubles caused by ultraviolet irradiation. As a result, they have found that the combined use of a bacterium belonging to *Streptococcus thermophilus* and a bacterium belonging to the genus *Bifidobacterium* synergistically enhances the skin property-improving effect brought about by each of them, whereby an excellent skin property-improving agent for oral administration is obtainable. They have completed the present invention on the basis of the above findings.

That is, the present invention provides a skin property-improving agent for oral administration containing, as an active ingredient, a bacterium belonging to the genus *Streptococcus* and a bacterium belonging to the genus *Bifidobacterium*, or fermented milk containing the two bacteria.

The present invention also provides a combination of a bacterium belonging to the genus *Streptococcus* and a bacterium belonging to the genus *Bifidobacterium* or fermented milk containing the two bacteria for use in improving a skin property by oral ingestion.

The present invention also provides a method for improving a skin property, comprising orally ingesting a bacterium belonging to the genus *Streptococcus* and a bacterium belonging to the genus *Bifidobacterium*, or fermented milk containing the two bacteria.

The present invention also provides use of a bacterium belonging to the genus *Streptococcus* and a bacterium belonging to the genus *Bifidobacterium*, or fermented milk containing the two bacteria for the manufacture of a skin property-improving agent for oral administration.

Effect of the Invention

The skin property-improving agent of the present invention markedly improves skin properties by oral ingestion. Namely, for example, the skin property-improving agent of the present invention has the actions of preventing a reduction in the water content of the stratum corneum caused particularly by ultraviolet irradiation or promoting an increase in the water content of the stratum corneum; improves the barrier function of the skin; improves the stratum corneum morphology (regularity of arrangement, clarity of cell morphology, and the like); inhibits thickening of the skin; inhibits the formation of wrinkles; inhibits an increase in transepidermal water loss; and has an action of increasing the activity of keratinization-related enzymes (cathepsin L-like activity). Also, the skin property-improving agent of the present invention contains a bacterium belonging to the genus *Streptococcus* and a bacterium belonging to the genus *Bifidobacterium*, both of which are orally ingestible, as the active ingredient. Thus, it is highly safe and continuous ingestion is made possible. Moreover, because these bacteria exert the aforementioned actions and effects regardless of their vital state (i.e., dead or alive), the dosage form of the skin property-improving agent of the present invention can be determined according to various preferences. Thus, the skin property-improving agent of the present invention is useful as an oral pharmaceutical product, a food, and a drink.

MODES FOR CARRYING OUT THE INVENTION

The skin property-improving agent for oral administration of the present invention contains, as an active ingredient, a bacterium belonging to the genus *Streptococcus* and a bacterium belonging to the genus *Bifidobacterium*, or fermented milk containing the two bacteria.

Examples of the bacterium belonging to the genus *Streptococcus* which can be used in the present invention include *Streptococcus thermophilus* (also referred to as *S. therm.*), *S. pyogenes, S. zooepidemicus, S. equi, S. equisimilis*, and *S. dysgalactiae*. From the viewpoint of the skin property-improving effect, *Streptococcus thermophilus* is preferable. Specific examples of *Streptococcus thermophilus* include *Streptococcus thermophilus* YIT 2021 (FERM BP-7537: date of deposition, Apr. 5, 2001), *Streptococcus thermophilus* YIT 2084 (FERM BP-10879: date of deposition, Jul. 24, 2007), and *Streptococcus thermophilus* YIT 2001 (FERM BP-7538: date of deposition, Apr. 5, 2001).

Examples of the bacterium belonging to the genus *Bifidobacterium* which can be used in the present invention include *Bifidobacterium breve* (also referred to as *B. breve.*), *B. longum, B. bifidum, B. animalis, B. suis, B. infantis, B. adolescentis, B. catenulatum, B. pseudocatenulatum, B. lactis*, and *B. globosum*. Among them, *Bifidobacterium breve, Bifidobacterium longum*, and *Bifidobacterium bifidum* have a long history of frequent use in dairy products, and their safety data and the like have been accumulated. Further, these bacteria are preferable from the viewpoint of the skin property-improving effect, and particularly, *Bifidobacterium breve* is preferable. Specific examples of *Bifidobacterium breve* include *Bifidobacterium breve* YIT 12272 (FERM BP-11320: date of deposition, Jan. 20, 2011) and *Bifidobacterium breve* YIT 4065 (FERM BP-6223: date of deposition, Jan. 16, 1998). The aforementioned *Streptococcus thermophilus* and *Bifidobacterium breve* have been deposited at International Patent Organism Depositary, The National Institute of Advanced Industrial Science and Technology, Tsukuba Central 6, 1-1-1 Higashi, Tsukuba, Ibaraki, 305-8566.

The aforementioned two bacteria can be used as the skin property-improving agent alive as-is, and in addition, for example, the freeze-dried product of viable bacteria, dead bacteria obtained by subjecting these bacteria to sterilization treatment such as heat treatment and alcohol treatment, a culture product containing the above bacteria, or further processed products of the above bacteria or culture product can be used as the skin property-improving agent.

The skin property-improving agent of the present invention markedly improves skin properties by oral ingestion. Namely, for example, the skin property-improving agent of the present invention has the actions of preventing a reduction in the water content of the stratum corneum caused particularly by ultraviolet irradiation or promoting an increase in the water content of the stratum corneum; improves the barrier function of the skin; improves the stratum corneum morphology (regularity of arrangement, clarity of cell morphology, and the like); inhibits thickening of the skin; inhibits the formation of wrinkles; inhibits an increase in transepidermal water loss; and has an action of increasing the activity of keratinization-related enzymes (cathepsin L-like activity).

In the present invention, prevention of a reduction in the water content of the stratum corneum caused by ultraviolet irradiation refers to, for example, an inhibitory action on the reduction of the water content of the stratum corneum caused by ultraviolet irradiation, which is confirmed by measuring the water content of the stratum corneum by the method demonstrated by Examples to be described later, and an action of promoting an increase in the water content of the stratum corneum refers to an action of promoting, irrespective of the presence or absence of ultraviolet irradiation, the water content of the stratum corneum to the same or a higher level than that of healthy skin which has not been exposed to ultraviolet radiation. Here, the method of measuring the water content of the stratum corneum is not limited to the method demonstrated by Examples to be described later.

For the purpose of enhancing the skin property-improving action, indigestible sugar can be further added to the skin property-improving agent of the present invention. As the indigestible sugar, an oligosaccharide such as galacto-oligosaccharide and fructo-oligosaccharide is preferable, and particularly, galacto-oligosaccharide is preferable. Although the dose per intake of the above indigestible sugar cannot be unconditionally determined because it varies also depending on the symptoms, age, body weight, etc. of an individual who ingests the skin property-improving agent, the dose can be set at about 0.1 to 10 g.

The skin property-improving agent of the present invention can be prepared as pharmaceutical products of various dosage forms with a pharmaceutically acceptable carrier by a routine method.

For example, to the aforementioned bacterial strains, processed products of those bacteria, and the like, added are an excipient such as lactose, sucrose, sodium chloride, glucose, urea, starch, calcium carbonate, kaolin, crystalline cellulose, and silicic acid, a binder such as water, ethanol, propanol, a glucose solution, a starch solution, a gelatin solution, carboxymethylcellulose, methylcellulose, potassium phosphate, and polyvinylpyrrolidone, a disintegrant such as sodium alginate, powdered catechin, sodium bicarbonate, calcium carbonate, polyoxyethylene sorbitan fatty acid esters, and sodium lauryl sulfate, a humectant such as glycerin and starch, a lubricant such as purified talc, a stearic acid salt, and polyethylene glycol, and the like, and then granules, tablets, capsules, and the like can be produced according to a routine method. Further, if necessary, tablets can be prepared as tablets having a usual coating such as sugar-coated tablets, gelatin-coated tablets, enteric coated tablets, film-coated tablets, or double layered tablets or multiple layered tablets.

While the skin property-improving agent for oral administration of the present invention contains a bacterium belonging to the genus *Streptococcus* and a bacterium belonging to the genus *Bifidobacterium*, fermented milk containing the two bacteria may also be used. As the fermented milk, one obtained by culturing the aforementioned two bacteria in a medium containing milk components may be used. The aforementioned two bacteria can be each separately cultured in the media containing milk components to produce fermented milk of each one of the bacteria, which can be mixed together later. Alternatively, the aforementioned two bacteria can be mixed and cultured together in the medium containing milk components.

As the milk component contained in the medium, animal milk such as cow milk and goat milk, defatted milk, powdered milk, defatted powdered milk, cream, and the like can be used. Culture may be performed in accordance with a routine production method of fermented milk, and for example, culture may be performed at 25 to 46° C., preferably at 35 to 42° C., for 6 to 120 hours, preferably for 24 to 72 hours. Culture can be performed by any method such as static culture, stirring culture, and shaking culture.

Further, by adding the aforementioned bacteria, processed products of those bacteria, or the like directly to foods, or when edible media such as milk components are used, by producing fermented food products such as fermented milk using the above bacterial strains, the skin property-improving agent of the present invention can be utilized as a variety of foods and drinks. Preferred examples of the foods and drinks include yogurt, cheese, fermented milk, dairy products, lactic acid drinks, fermented soy milk, ice cream, fruit juice drinks, soup, and cookies.

The skin property-improving agent of the present invention can contain, particularly when it is in the form of fermented milk, various routinely-employed food materials. Specific examples thereof include sugar such as sucrose, glucose, fructose, palatinose, trehalose, lactose, xylose, and maltose, sugar alcohol such as sorbitol, xylitol, erythritol, lactitol, palatinit, reduced sugar syrup, and reduced malt sugar syrup, high intensity sweeteners such as aspartame, thaumatin, sucralose, acesulfame K, and stevia, various kinds of viscosity stabilizers such as agar, gelatin, carrageenan, guar gum, xanthan gum, pectin, locust bean gum, gellan gum, carboxymethylcellulose, soybean polysaccharides, and propylene glycol alginate, emulsifiers such as sucrose fatty acid ester, glycerol fatty acid ester, polyglycerol fatty acid ester, sorbitan fatty acid ester, and lecithin, milk fat such as cream, butter, and sour cream, and mineral components such as calcium, magnesium, zinc, iron, and manganese.

Also, the skin property-improving agent of the present invention can contain materials which have beneficial effects on skin properties by oral ingestion. Examples of such a material include vitamins such as vitamin A, vitamin Bs, vitamin C, vitamin D, and vitamin E, carotenoid such as β-carotene, γ-carotene, and lutein, fatty acids such as linoleic acid, linolenic acid, EPA, and DHA, skin components such as collagen, mucopolysaccharides, and ceramide.

Further, the skin property-improving agent of the present invention may contain an orally-ingestible lactic acid bacterium which impart beneficial functions to the living body.

Examples of such a lactic acid bacterium include bacteria belonging to the genus *Lactobacillus* such as *Lactobacillus acidophilus, Lactobacillus brevis, Lactobacillus coryniformis, Lactobacillus curvatus, Lactobacillus casei, Lactobacillus delbrueckii* subsp. *lactis, Lactobacillus delbrueckii* subsp. *bulgaricus, Lactobacillus fermentum, Lactobacillus gallinarum, Lactobacillus gasseri, Lactobacillus helveticus, Lactobacillus johnsonii, Lactobacillus kefiri, Lactobacillus mali, Lactobacillus plantarum, Lactobacillus pentosus, Lactobacillus paracasei, Lactobacillus sakei,* and *Lactobacillus zeae*, bacteria belonging to the genus *Lactococcus* such as *Lactococcus lactis* subsp. *lactis, Lactococcus lactis* subsp. *cremoris,* and *Lactococcus plantarum*, bacteria belonging to the genus *Leuconostoc* such as *Leuconostoc mesenteroides* subsp. *cremoris,* and *Leuconostoc lactis,* and bacteria belonging to the genus *Pediococcus* such as *Pediococcus acidilactici, Pediococcus pentosaceus,* and *Pediococcus halophilus,* and bacteria belonging to the genus *Enterococcus* such as *Enterococcus faecium* and *Enterococcus faecalis*. These bacteria can be used alone or in combination of two or more of them.

Although the dose per intake of a bacterium belonging to the genus *Streptococcus* and a bacterium belonging to the genus *Bifidobacterium* in the orally ingestible skin property-improving agent of the present invention cannot be unconditionally determined because it varies also depending on the symptoms, age, body weight, etc. of an individual who ingests the skin property-improving agent, the dose per intake of each of the above bacteria may be about $10^3$ to $10^{13}$ CFU, particularly preferably about $10^6$ to $10^{13}$ CFU in terms of bacterial count.

Also, the timing of the initiation of ingestion, the ingestion period, and the like of the skin property-improving agent of the present invention are not particularly limited, and it may be orally ingested before and/or after the development of skin disorder associated with ultraviolet irradiation. However, in order to achieve sufficient effects, it is preferably ingested orally continuously irrespective of the presence or absence of the development of skin disorder associated with ultraviolet irradiation, and the like.

EXAMPLES

Hereinafter, the present invention will be further described in detail with reference to Examples; however, the present invention is not limited in any way by these Examples.

Reference Example 1

Breeding for the Improvement of *Bifidobacterium breve* YIT 10001 and YIT 4125 by the Alternate Subculture Method Using *Bifidobacterium breve* YIT 10001 (FERM BP-8205) and *Bifidobacterium breve* YIT 4125 (FERM BP-7813) as the parent strains, bacteria were concentrated by alternate subculture.

(1) After sterilizing a 20.7% whole milk powder medium at 135° C. for 3.5 seconds, a seed starter 1 of the *Bifidobacterium breve* YIT 10001 or YIT 4125 was inoculated at 0.5% and a seed starter of *Bifidobacterium bifidum* was seeded at 1%, and the bacteria were cultured together at 33° C. until the pH reached 5.3, whereby a bacterial solution A1 (400 mL) was prepared.

(2) Into the bacterial solution A1, a syrup solution A was blended so that the final concentration of palatinose was 10%, whereby a dairy product A1 (630 mL) was prepared. The dairy product A1 (200 mL) was dispensed into 300-mL flasks, which were closed with cotton plugs. Under such an aerobic condition, the bacteria were stored at 5° C. for one week while stirring (90 rpm) (hereinafter, abbreviated as aerobic stirring storage). Subsequently, the resulting dairy product A1 was poured into test tubes to full height, which were plugged with butyl rubber, and under such an anaerobic condition, the bacteria were left to stand at 10° C. for one week (hereinafter, abbreviated as anaerobic static storage).

(3) The dairy product A1 (1 mL) stored under the above conditions was inoculated in 10 ml of a cephalothin-added milk medium (12% defatted powdered milk, 0.1% yeast extract, 0.03% L-cysteine hydrochloride, 0.2% sedimentary calcium carbonate, and 5 μg/mL cephalothin, hereinafter abbreviated as a cephalothin-added milk medium), followed by anaerobic culture at 37° C. for 24 hours, whereby a mother starter 2 of *Bifidobacterium breve* was prepared. The mother starter 2 (0.03 mL) was inoculated in 30 mL of a milk medium (12% defatted powdered milk, 0.1% yeast extract, 0.03% L-cysteine hydrochloride, and 0.2% sedimentary calcium carbonate, hereinafter, abbreviated as a milk medium), followed by anaerobic culture at 37° C. for 24 hours, whereby a seed starter 2 of *Bifidobacterium breve* was prepared. Using the seed starter 2, similar operations to the above were repeated. That is, a dairy product A2 prepared from the seed starter 2 was subjected to aerobic stirring storage, and then to anaerobic static storage, whereby a mother starter 3, and further, a seed starter 3 of *Bifidobacterium breve* were prepared.

(4) Subsequently, a 23.5% defatted powdered milk medium was sterilized at 120° C. for 3.5 seconds, and the seed starter 3 of *Bifidobacterium breve* was inoculated at 2% and the seed starter of *Lactococcus lactis* was inoculated at 0.01%, and the bacteria were cultured together at 37° C. until the pH reached 4.4, whereby a bacterial solution B1 (100 mL) was prepared.

(5) Also, a 19.7% defatted powdered milk medium was sterilized at 120° C. for 3.5 seconds, to which milk peptide was added at 0.08%. Into this medium, a seed starter of *Streptococcus thermophilus* was inoculated at 0.5% and cultured at 37° C. until the pH reached 4.3, whereby a bacterial solution C1 (700 mL) was prepared. The bacterial solution C1 was added to the bacterial solution B1 (at a mixing ratio of 1:2), and further, a syrup solution B was blended so that the final concentration of reduced malt sugar syrup was 5%, whereby a dairy product B1 (870 mL) was prepared.

(6) Similarly to the dairy product A1, the dairy product B1 (1 mL) was subjected to aerobic stirring storage, and then to anaerobic static storage. The resulting dairy product B1 was inoculated into 10 mL of a cephalothin-added milk medium, followed by anaerobic culture at 37° C. for 24 hours, whereby a mother starter 4 of *Bifidobacterium breve* was prepared. The mother starter 4 (0.03 mL) was inoculated into 30 mL of the milk medium, followed by anaerobic culture at 37° C. for 24 hours, whereby a seed starter 4 of *Bifidobacterium breve* was prepared. Using the seed starter 4, similar operations to the above were repeated. That is, the dairy product B2 prepared from the seed starter 4 was subjected to aerobic stirring storage, and then to anaerobic static storage, whereby a mother starter 5, and further, a seed starter 5 of *Bifidobacterium breve* were prepared.

As described above, preparation, aerobic stirring storage, and anaerobic static storage of the dairy product A were repeated twice. Subsequently, using the surviving *Bifidobacterium breve*, preparation, aerobic stirring storage, and anaerobic static storage of the dairy product B were repeated twice, whereby concentration operations of *Bifidobacterium breve* were performed. Setting a series of the above procedures at one cycle, a total of four cycles were repeated. Finally, the dairy products A8 and B8 were subjected to anaerobic static storage at 10° C. for two weeks, and 1 mL of each was spread onto a 5 μg/mL cephalothin-added TOS propionic acid agar medium (Yakult Pharmaceutical Industry Co., Ltd.) and anaerobically cultured at 37° C. using Anaero Pack (Mitsubishi Gas Chemical Company, Inc.), whereby colonies were isolated. By repeating the above colony isolation for purification, a total of 21 strains from the dairy products A8 and a total of 21 strains from the dairy products B8 were isolated, respectively, as single colonies derived from the *Bifidobacterium breve* YIT 10001 and YIT 4125, resulting in a total of 42 isolated strains.

Reference Example 2

Viability Confirmation Test

Using the parent strains and isolated strains, the dairy products A and B were each prepared by the method of Reference Example 1, and stored under aerobic conditions at 5° C. for one week while stirring, and then left to stand under anaerobic conditions at 10° C. for two weeks. Then, *Bifidobacterium breve* YIT 12272 (derived from the YIT 4125 strain, isolated from the dairy product A8) was selected, which exhibited good viability in both of the dairy products A and B.

The results of the viability of the YIT 12272 strain and the control bacteria (the YIT 10001 strain and YIT 4125 strain) in the dairy products A and B are shown in Table 1. Regarding the YIT 12272 strain, $3 \times 10^7$ cfu/mL or more surviving cells were observed in both of the dairy products A and B even after stirring storage under aerobic conditions at 5° C. for one week and the successive static storage under anaerobic conditions at 10° C. for two weeks. In contrast, although $3 \times 10^7$ cfu/mL or more surviving cells were observed in either one of the dairy products A and B prepared using the control bacteria, these bacteria did not show good viability in both of the products.

Also, the physical properties of the dairy products A and B are shown in Table 2. The dairy product A was prepared by blending the syrup A into the bacterial solution A, and the pH and acidity of the diary product A were found to be 5.6 and 3.4, respectively. While the osmotic pressure of the bacterial solution A was 550 mOsm, that of the dairy product A was increased to 950 mOsm. Meanwhile, the dairy product B was prepared by blending the bacterial solution C and the syrup B into the bacterial solution B, and the pH and acidity of the dairy product B were found to be 4.4 and 7.5, respectively. While the osmotic pressure of the bacterial solution B was 900 mOsm, that of the dairy product B was decreased to 600 mOsm.

From the above findings, it was revealed that, compared to the control bacteria, the viability of the *Bifidobacterium breve* YIT 12272 was enhanced in both of the dairy products A and B, which differed in culture temperature, pH, acidity, changes in osmotic pressure due to blending of syrup, a nonfat milk solid content, and a milk fat content.

TABLE 1

*Bifidobacterium* breve after storage in
the dairy products A and B
Viable cell count of YIT 12272 strain

| | Viable cell count (cfu/mL) | |
|---|---|---|
| | Dairy product A | Dairy product B |
| Test bacteria | | |
| YIT 12272 strain | $1.2 \times 10^8$ | $5.8 \times 10^7$ |
| Control bacteria | | |
| YIT 10001 strain | $6.0 \times 10^6$ | $4.1 \times 10^7$ |
| YIT 4125 strain | $1.0 \times 10^8$ | $6.0 \times 10^6$ |

Viable cell count was measured on a 5 μg/mL cephalothin-added TOS propionic acid agar medium after stirring storage under aerobic conditions at 5° C. for one week and the successive static storage under anaerobic conditions at 10° C. for two weeks.

TABLE 2

Physical properties of the dairy products A and B

|  | Dairy product A | | Dairy product B | |
| --- | --- | --- | --- | --- |
|  | Bacterial solution A | Product | Bacterial solution B | Product |
| Culture temperature (° C.) | 33 | | 37 | |
| pH | 5.3 | 5.6 | 4.4 | 4.4 |
| Acidity | 6.0 | 3.4 | 20.7 | 7.5 |
| Osmotic pressure (mOsm) | 550 | 950 | 900 | 600 |
| Nonfat milk solid content (%) | 14.5 | 9.4 | 22.4 | 8.9 |
| Milk fat content (%) | 5.2 | 3.4 | 0.2 | 0.1 |

Osmotic pressure was measured using osmostat OM-6040 manufactured by Kyoto Daiichi Kagaku Co., Ltd.

Example 1

(1) Experimental Animal and Rearing Method

Five-week-old female hairless mice (Hos: HR-1) were used. The mice were reared in a group in a CS cage. After accustoming the mice to AIN93G diet for one week, they were grouped so that there was no difference in body weight, and then reared on the test diet for two weeks. The experiment was conducted under the rearing conditions of a constant temperature of 24±1° C. and a constant humidity of 60±5% throughout the experimental period, and the light-dark cycle was 12 hours. The mice were given diet and water ad libitum. The diet was produced by modifying the composition of AIN93G. The diet was mixed in a mortar, to which an appropriate amount of deionized water was added to prepare a paste, which was then transferred to a freeze-drying tray and cut into blocks. After freeze-drying, the diet was vacuum-packed and refrigerated. The composition of the diet is shown in Table 3.

TABLE 3

|  | Control | Fermented milk |
| --- | --- | --- |
| Corn starch | 26.75 | 26.75 |
| Casein | 13.2 | 13.2 |
| Dextrin | 13.2 | 13.2 |
| Sucrose | 10 | 10 |
| Corn oil | 6.8 | 6.8 |
| Cellulose | 5 | 5 |
| Mineral mixture AIN93 | 3.5 | 3.5 |
| Vitamin mixture AIN93 | 1 | 1 |
| L-cysteine | 0.3 | 0.3 |
| Choline bitartrate | 0.25 | 0.25 |
| Defatted powdered milk | 20 | 0 |
| Fermented milk | 0 | 20 |
|  | 100% | 100% |

(2) Experimental Group

TABLE 4

| Group | UV | n Number of mice | Diet |
| --- | --- | --- | --- |
| Blank | − | 5 | Unfermented milk (defatted powdered milk) (20%) |
| Control | + | 5 | " |
| Powdered B. breve | + | 5 | " + B. breve bacteria |
| B. breve Fermented milk | + | 5 | Fermented milk (20%) |
| S. therm. Fermented milk | + | 5 | " |
| B. breve + S. therm. mixed fermented milk | + | 5 | B. breve Fermented milk (10%) + S. therm. Fermented milk (10%) |

B. breve: Bifidobacterium breve YIT12272
S. therm: Streptococcus thermophilus YIT2084

(3) Test Diet (a) Powdered B. breve . . . . A m-ILS liquid medium was prepared according to a routine method, followed by sterilization treatment at 121° C. for 15 minutes. Then, the seed starter was inoculated at 1% under the condition of replacing the gas phase by $N_2$, followed by culture at 37° C. for 23 hours. The viable cell count right after the culture was $1.16 \times 10^9$ CFU/mL. The culture liquid thus obtained was washed with physiological saline and the medium components were removed, and the resulting product was mixed with the modified AIN-93G diet. After mixing, the resulting product was freeze-dried, whereby a solid diet was produced.

(b) B. breve. fermented milk . . . . A medium was prepared by adding 0.03% yeast extract to 10% defatted powdered milk (YOTSUBA YAA), followed by sterilization treatment at 121° C. for 15 minutes. Then, the seed starter prepared in accordance with a routine method was inoculated at 1% under the condition of replacing the gas phase by $N_2$, followed by culture at 37° C. for 44 hours. The viable cell count right after the culture was $1.02 \times 10^8$ CFU/mL. The culture liquid thus obtained was powderized by freeze-drying and mixed with the diet. After mixing, the resulting product was freeze-dried, whereby a solid diet was produced.

(c) S. therm. fermented milk . . . . In 10% defatted powdered milk, the seed starter was inoculated at 0.1%, to which separately-sterilized Hinute DH (Fuji Oil Co., Ltd.) was added, followed by culture for 24 hours at 37° C., 100 rpm, and pH 6.8 in a jar fermentor (B. E. Marubishi Co., Ltd.). The viable cell count right after the culture was $5 \times 10^8$ CFU/mL. The culture liquid thus obtained was powderized by freeze-drying, and then mixed with the diet. After mixing, the resulting product was freeze-dried, whereby a solid diet was produced.

(d) B. breve+S. therm. mixed fermented milk . . . . The B. breve fermented milk and S. therm. fermented milk, both of which were cultured and then powderized by the aforementioned method, were each added at 10%, whereby a diet was prepared.

(4) Cell Count Measurement Method

The diet was homogenized in a mortar and appropriately diluted with sterilized 0.1% Bacto yeast extract (manufactured by Difco), and spread onto an agar plate medium. Subsequently, the viable cell count was measured.

(5) Experimental Schedule

From day 11 of the ingestion of the test diet, ultraviolet irradiation was performed for four days at 40 mJ/cm$^2$/day using an ultraviolet irradiation device (Toshiba SE-FL-20), and dissection was performed on the following day. Body weight was measured once per week, and the amount of diet intake was measured twice to three times a week, and other than that, the mice were observed for daily activities.

(6) Measurement Items

On day 15 after the initiation of the test diet, the skin properties were measured using a skin measurement apparatus.
(A) Transepidermal Water Loss (TEWL)
Using Tewa meter TM210 (Courage+khazaka electronic GmbH), transepidermal water loss was measured and the value thus obtained was used as an index of barrier function. The value indicates an average of the values obtained by conducting the measurement for 30 seconds, every two seconds.
(B) Water Content of the Stratum Corneum
Using a 3.5 MHZ high-frequency conductance measurement device (SKICON-200, IBS), the conductance value of the stratum corneum of the mouse dorsal skin was measured.

(7) Statistics

Statistical processing was performed using the SAS Preclinical Package, and for significance test, Dunnett test was performed.

Figure 1:
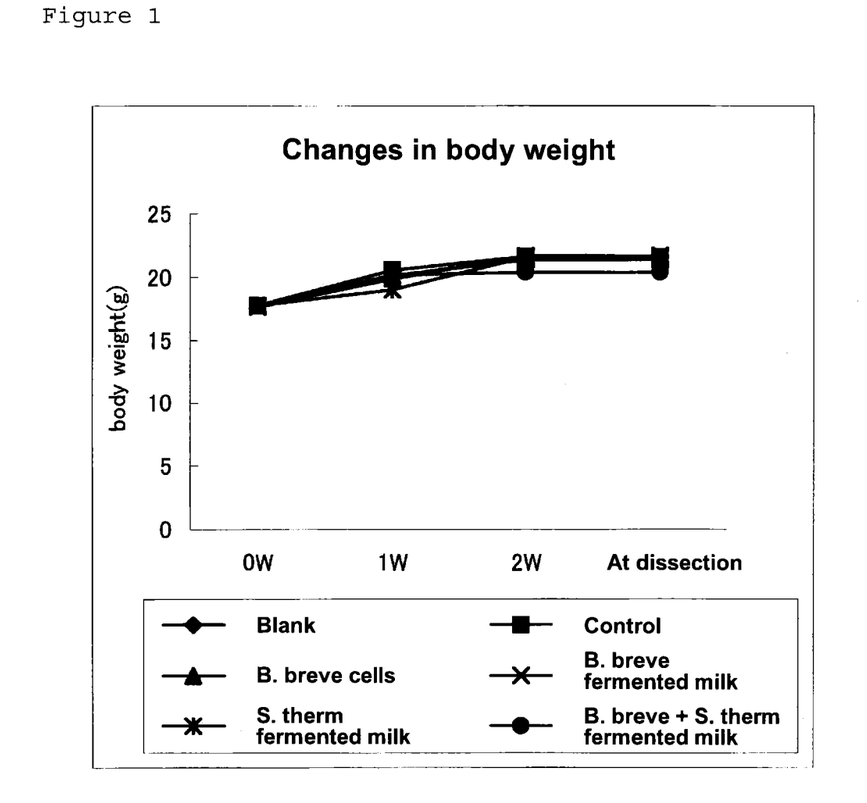
FIG. 1 is a graph showing the changes in body weight in each test group.
Figure 2:
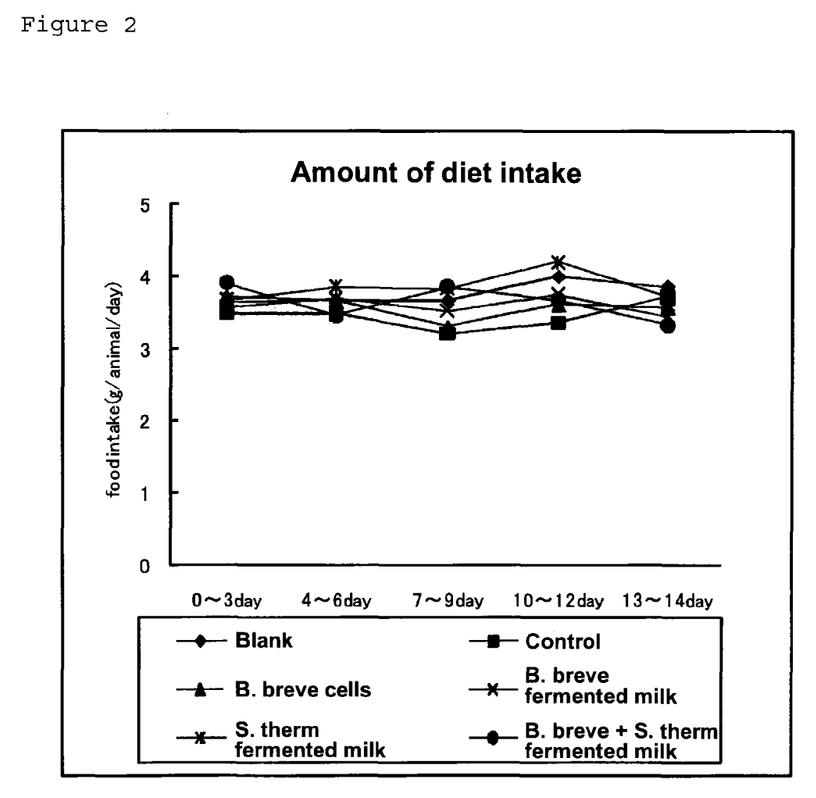
FIG. 2 is a graph showing the changes in food intake in each test group.
Figure 3:
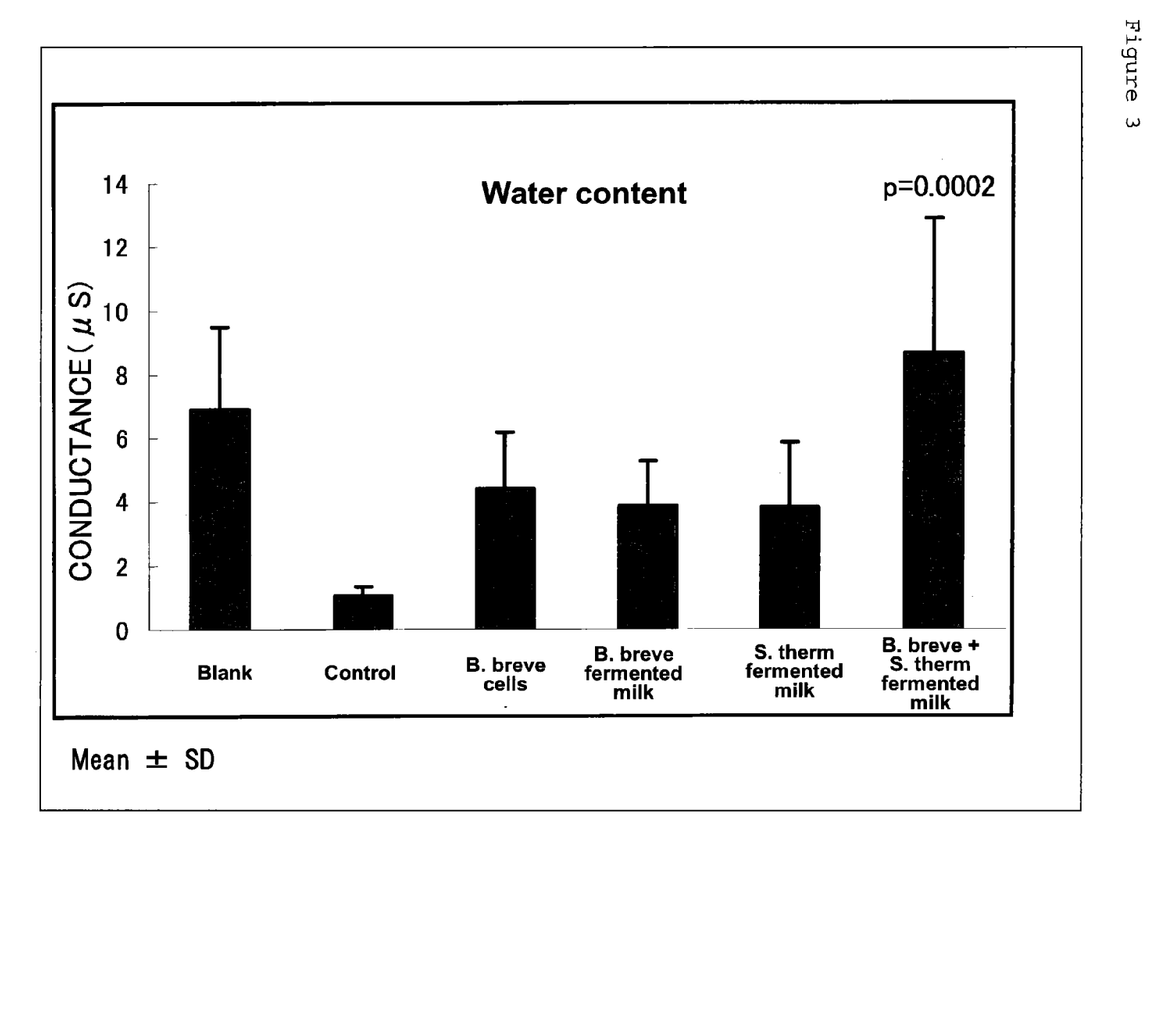
FIG. 3 is a graph showing the water content of the stratum corneum in each test group.
Figure 4:
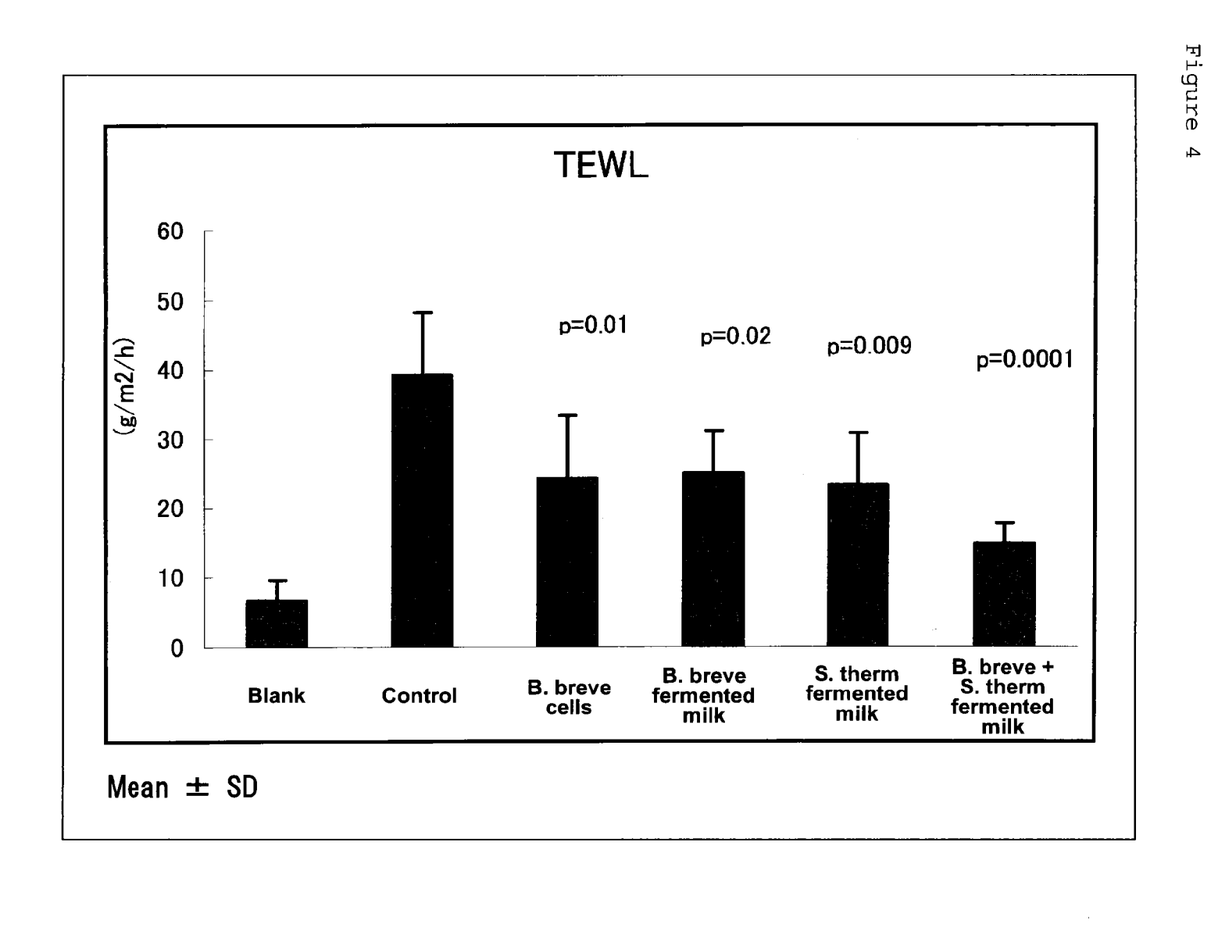
FIG. 4 is a graph showing the transepidermal water loss in each test group.

8 a. Body Weight and Amount of Diet Intake
The time-dependent changes in the body weight and amount of diet intake are shown in FIGS. 1 and 2. No significant difference was observed between any of the groups, and differences in the growth and health condition of the mice attributable to ultraviolet irradiation and differences in samples were not observed.
(B) Skin Properties
b-1. Water Content of the Stratum Corneum
The water content of the stratum corneum is shown in FIG. 3. Although the water content of the stratum corneum was markedly decreased due to ultraviolet irradiation, the decrease was significantly inhibited in the group given the *Bifidobacterium breve* and *Streptococcus thermophilus* mixed fermented milk. The results were synergistic relative to the group given either one of *Bifidobacterium breve* and *Streptococcus thermophilus* alone. The results even exceeded the results of the blank group given no ultraviolet irradiation, showing an extremely remarkable effect. That is, the skin property-improving agent of the present invention not only simply inhibits a decrease in the water content of the stratum corneum caused by ultraviolet irradiation, but also has an action of promoting an increase in the water content of the stratum corneum to the same or a higher level than that of healthy skin which has not been exposed to ultraviolet radiation, indicating that the skin property-improving agent of the present invention has extremely high practical utility.

b-2. Transepidermal Water Loss (TEWL)
TEWL is shown in FIG. 4. TEWL was greatly accelerated by ultraviolet irradiation, suggesting reduced epidermal barrier function. A reduction in the epidermal barrier function was significantly improved in all groups. This epidermal barrier function-improving effect was the highest in the group given the *Bifidobacterium breve* and *Streptococcus thermophilus* mixed fermented milk.

Example 2

(1) Production of Fermented Milk Containing *Bifidobacterium breve* YIT 12272 and *Streptococcus thermophilus* YIT 2021

Into a defatted powdered milk solution (SNF 20.7%) which was subjected to plate sterilization at 120° C. for 3.5 seconds, the pre-culture solution of *Bifidobacterium breve* YIT 12272 was inoculated at 2%, followed by 24 hours of culture at 37° C. to obtain bifidobacteria fermented milk. Also, into a defatted powdered milk solution (SNF 17.4%) which was similarly subjected to plate sterilization, the pre-culture solution of *Streptococcus thermophilus* YIT 2021 was inoculated at 0.5%, followed by 24 hours of culture at 37° C. to obtain lactic acid bacteria fermented milk. The resulting bacterial solutions were mixed, into which a syrup solution, which was a mixture of reduced malt sugar syrup, polydextrose, galacto-oligosaccharide, emulsified iron, aspartame, and the like, was blended, whereby fermented milk was obtained.

As placebo, unfermented milk containing neither the aforementioned bacteria nor galacto-oligosaccharide was produced. To the unfermented milk, lactic acid and acetic acid were added in equal amounts to the aforementioned fermented milk.

The composition of each drink is shown in Table 5. The average viable cell count of YIT 12272 and the average total bacterial count of lactic acid bacteria in the test drink at the initiation of drinking were $6.9 \times 10^8$ CFU/mL and $5.1 \times 10^8$ CFU/mL, respectively. Also, the average viable cell count of YIT 12272 and the average total bacterial count of lactic acid bacteria upon completion of drinking were $6.6 \times 10^8$ CFU/mL and $5.1 \times 10^8$ CFU/mL, respectively.

TABLE 5

|  | Test drink | Placebo |
| --- | --- | --- |
| Nonfat milk solid content (%) | 8.1 | 8.1 |
| Milk fat content (%) | 0.1 | 0.1 |
| Total solid content (%) | 16.4 | 16.4 |
| Degree of sweetness of product (%) | 60 | 60 |
| Per drink (100 mL) | | |
| Calories (kcal) | 48 | 58 |
| Protein (g) | 3.1 | 3.1 |
| Fat (g) | 0.1 | 0.1 |
| Carbohydrate (g) | 10.5 | 12.7 |
| Dietary fiber (g) | 2.5 | 0.2 |
| Galacto-oligosaccharide (g) | 0.6 | 0.0 |

(2) The subjects (females) in the placebo group and study group, 20 each, drank respective drinks every day for four weeks, one drink (100 mL) per day. The skin properties were evaluated before drinking, after drinking, and after post-observation (two weeks after the completion of drinking).

For the measurement of the skin, the subjects removed makeup by washing their faces with cleansing cream, and were kept in a relaxed state for 30 minutes to naturalize the skin. Then, the subjects lied down on the bed on their back, and the water content of the stratum corneum in the left cheek (the intersection point of the corner of an eye and the nose) was measured using Corneometer™ CM825 (manufactured by Integral Corporation) and SKICON-200 (manufactured by IBS, Co., Ltd.). Measurement was conducted five times and the resulting values were averaged out. Also, the water loss from the left cheek was measured using Cutometer MPA 580™ (manufactured by Integral Corporation).

For the measurement of wrinkles, a negative replica was produced from the corner of the left eye of the subject using silicon rubber (SILFLO, Flexico Developments), and the image of this replica was captured by a digital microscope, and then analyzed (WinROOF Pro Ver. 6.1: Mitani Corporation). The wrinkles were analyzed according to the guidance for wrinkle measurement prepared by Japan Cosmetic Industry Association and expressed in terms of the maximum depth of wrinkles (mm) as the measurement parameter.

As the index of the normalization of skin turnover, cathepsin L-like activity, wherein cathepsin L is a keratinization-related enzyme, was measured. As a method, fluorescence analysis using the synthetic peptide, Z-Val-Val-Arg-MCA, as a substrate was performed in accordance with a routine method.

For collection of the stratum corneum, the same part was selected before drinking and after post-observation, and after drinking, a part different from that selected before drinking was selected. In each of the above parts, three layers were collected from the same part by the tape stripping method. The collected sample of the second layer of the stratum corneum was stained in an aqueous solution of 0.5% brilliant green-1.0% gentian violet B at room temperature for eight minutes, followed by washing with distilled water. The image of the stained sample was captured by a digital microscope, and using the aforementioned image analysis device, the area of corneocyte, degree of roundness, and perimeter were measured. The area of 30 corneocytes was measured from three fields of vision per subject. Also, the stratum corneum morphology, namely regularity of arrangement and clarity of cell morphology, were each scored according to the evaluation criteria shown in Tables 6 and 7, and scores of three observers were averaged out.

TABLE 6

Evaluation criteria for regularity of arrangement

| Score | Criteria |
|---|---|
| 1 | There are very few regular colonies |
| 2 | There are many irregular colonies |
| 3 | There are many regular colonies |
| 4 | Most are regular colonies |

TABLE 7

Evaluation criteria for clarity of cell morphology

| Score | Criteria |
|---|---|
| 1 | Most are cells with unclear edge |
| 2 | Many are cells with unclear edge |
| 3 | Many are cells with clear edge |
| 4 | Most are cells with clear edge |

(3) Results
3-1. Water Content of the Stratum Corneum

Figure 5:
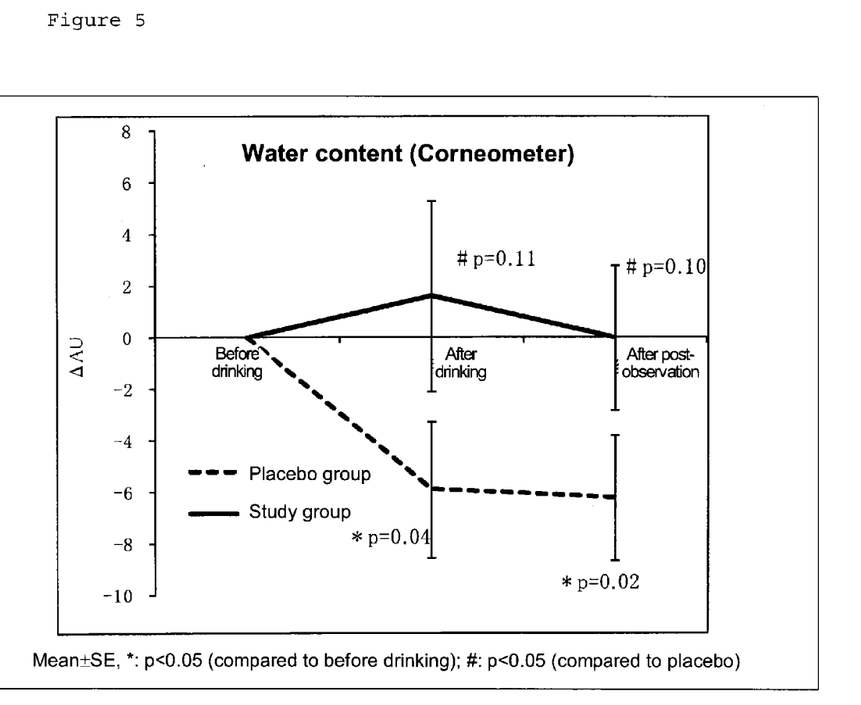
FIG. 5 is a graph showing the changes in the water content of the stratum corneum (measured by Corneometer) before and after drinking in humans.
Figure 6:
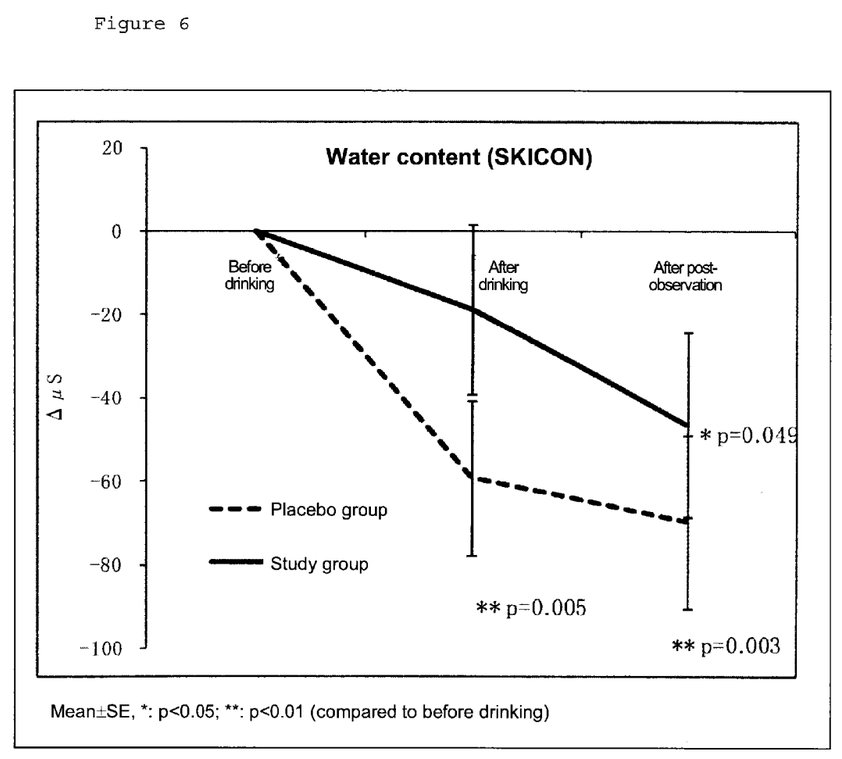
FIG. 6 is a graph showing the changes in the water content of the stratum corneum (measured by SKICON) before and after drinking in humans.

The shifts in the water content of the stratum corneum are shown in FIGS. 5 and 6. As a result of measurement by SKICON, in the placebo group, the water content of the stratum corneum was significantly decreased after drinking and after post-observation compared to before drinking. Meanwhile, in the study group, the water content of the stratum corneum did not change after drinking but was significantly decreased after post-observation. As a result of measurement by CORNEOMETER, in the placebo group, the water content of the stratum corneum was significantly decreased after drinking as well as after post-observation; however, in the study group, there was no change compared to before drinking. Also comparing the study group with the placebo group, although there was no significant difference, the study group showed higher values after drinking and after post-observation.

3-2. Keratinization-Related Enzyme

In the study group, compared to before drinking, the cathepsin L-like activity was significantly increased after drinking. Meanwhile, no change was observed in the placebo group.

3-3. Stratum Corneum Morphology

Figure 7:
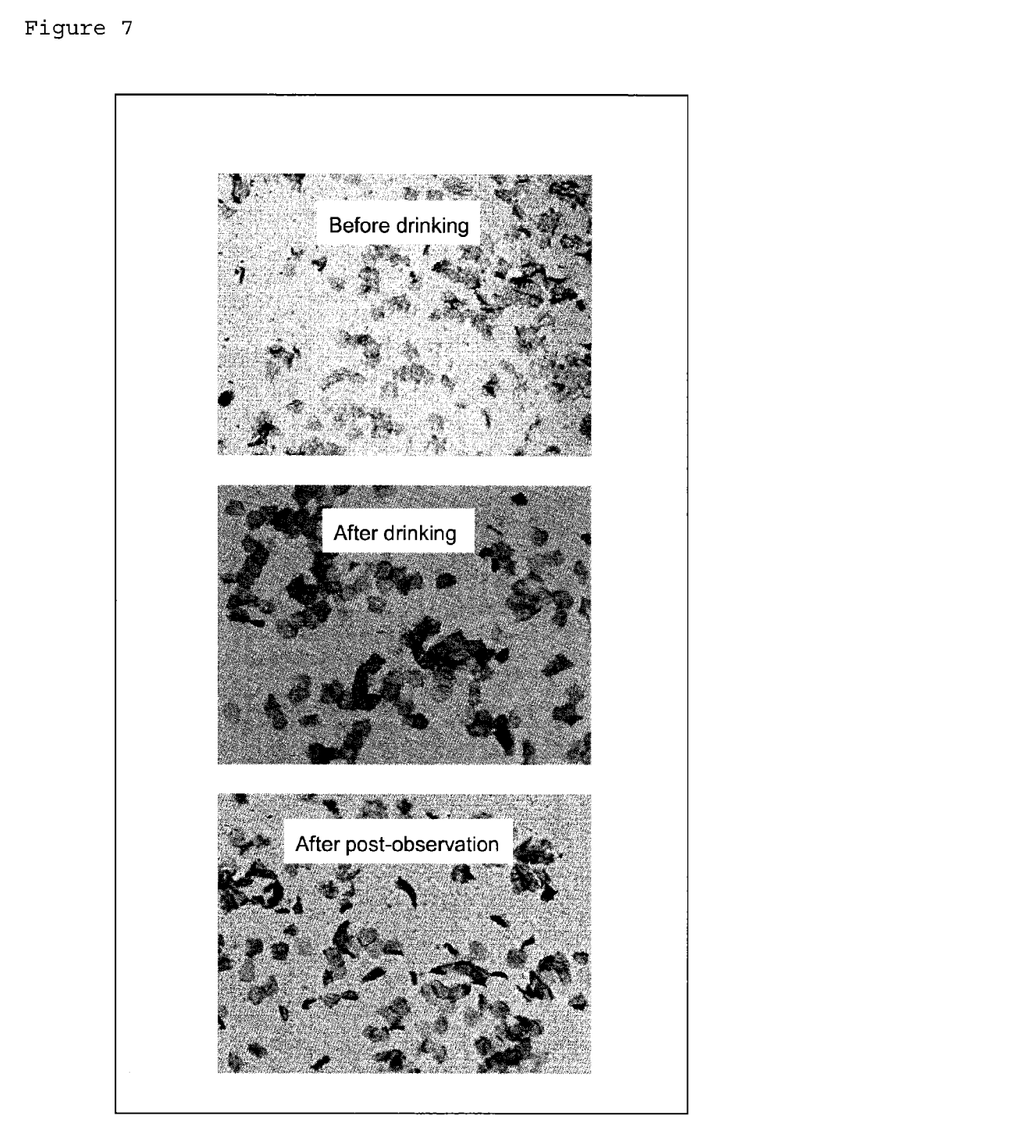
FIG. 7 is a diagram showing images of staining of human stratum corneum cells.

The shifts in the area of corneocyte, perimeter, and degree of roundness ($4\pi \times$area/(perimeter)$^2$, 0<degree of roundness≤1) were studied. As to the stratum corneum cell morphology, the cells are in a good condition when they are bigger and closer to a circle (regular hexagon). In light of this, with respect to any of the measurement parameters, it is determined that the larger the value, the better the condition of the stratum corneum. In both groups, compared to before drinking, the degree of roundness was significantly increased after drinking and after post-observation. As one example, the stained image of the stratum corneum cell of a woman in her 50s in the study group is shown in FIG. 7. It was observed that although the cells were small and had non-uniform shapes before drinking, they became large and were in a well-shaped (regular hexagon) state after drinking.

Figure 8:
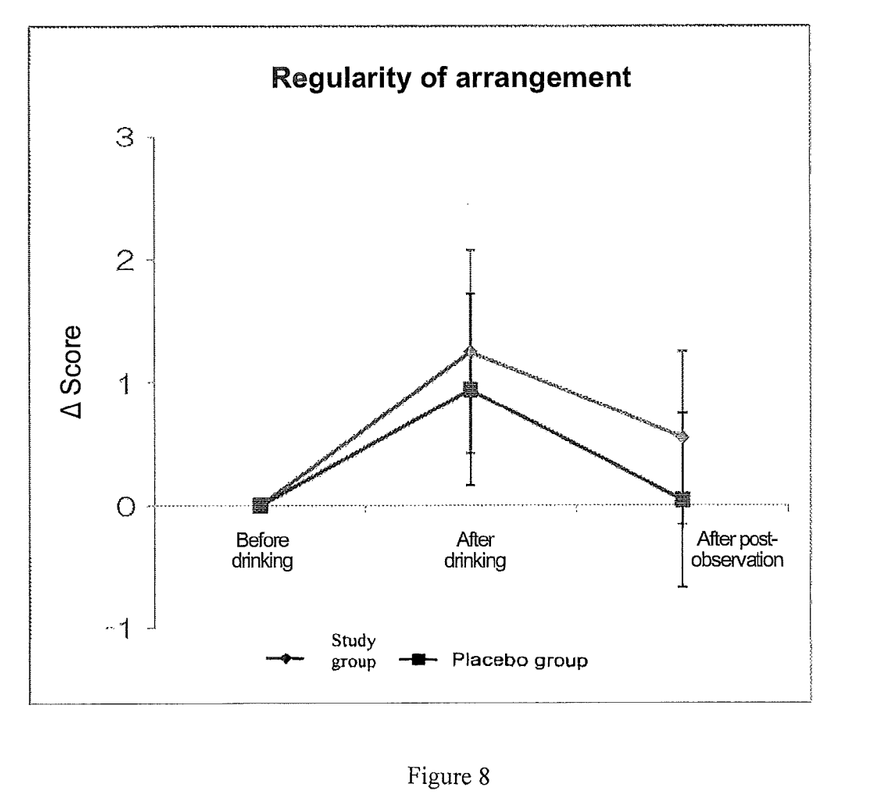
FIG. 8 is a graph showing a score shift in stratum corneum morphology (regularity of arrangement).
Figure 9:
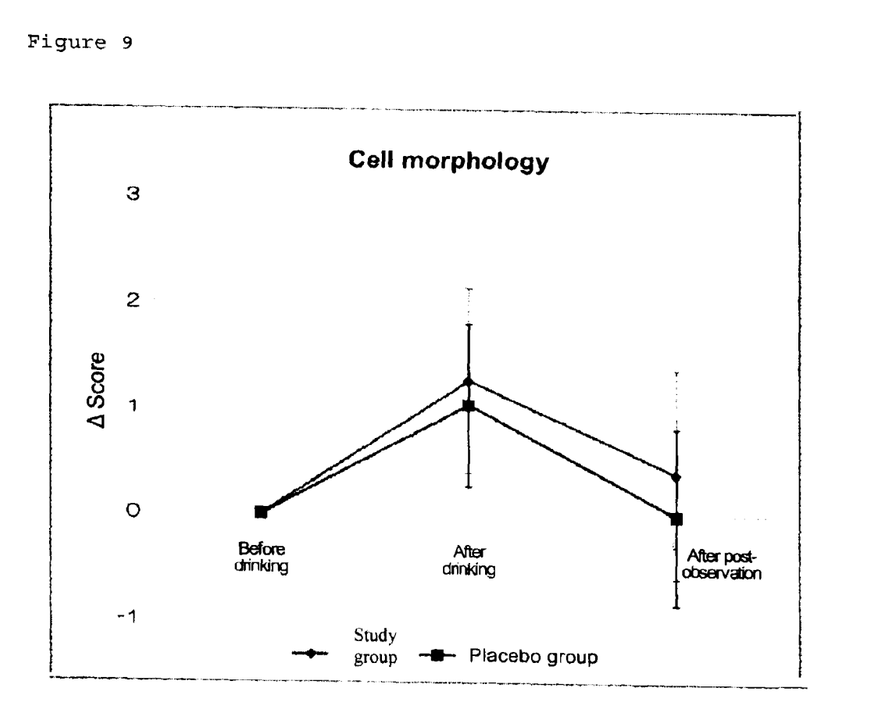
FIG. 9 is a graph showing a score shift in stratum corneum morphology (clarity of cell morphology).

The stratum corneum morphology (regularity of arrangement and clarity of cell morphology) was scored and evaluated, and the results thus obtained (the score value is expressed in terms of the amount of change (A score) relative to before drinking) are shown in FIGS. 8 and 9. Compared to the placebo group, in the study group, a score-improving effect was higher after drinking, and also, a tendency was observed that an ameliorating effect brought about by drinking was persistent even after post-observation.

3-4. Wrinkles

Although the maximum depth of wrinkles did not change in the placebo group, it was significantly decreased compared to before drinking in the study group.

Example 3

Production of Fermented Milk Containing *Bifidobacterium breve* YIT 4065 and *Streptococcus thermophilus* YIT 2021

Into a defatted powdered milk solution (SNF 20.7%) which was subjected to plate sterilization at 120° C. for 3.5 seconds, the pre-culture solution of *Bifidobacterium breve* YIT 4065 was inoculated at 2%, followed by 24 hours of culture at 37° C. to obtain bifidobacteria fermented milk. Also, into a defatted powdered milk solution (SNF 17.4%) which was similarly subjected to plate sterilization, the pre-culture solution of *Streptococcus thermophilus* YIT 2021 was inoculated at 0.5%, followed by 24 hours of culture at 37° C. to obtain lactic acid bacteria fermented milk. The resulting bacterial solutions were mixed, into which a syrup solution, which was a mixture of reduced malt sugar syrup, polydextrose, galacto-oligosaccharide, emulsified iron, aspartame, and the like, was blended, whereby fermented milk was obtained.

It has been confirmed that *Bifidobacterium breve* YIT 4065 exerts equivalent effects to *Bifidobacterium breve* YIT 12272 in terms of the skin property-improving action by oral ingestion (i.e., TEWL, water content, the number of sulcus cutis and crista cutis, and the like), and thus the fermented milk of the present Example is expected to have the skin property-improving action of the present invention.

Example 4

Production of Fermented Milk Containing *Bifidobacterium breve* YIT 4065 and *Streptococcus thermophilus* YIT 2084

Into a defatted powdered milk solution (SNF 20.7%) which was subjected to plate sterilization at 120° C. for 3.5 seconds, the pre-culture solution of *Bifidobacterium breve* YIT 4065 was inoculated at 2%, followed by 24 hours of culture at 37° C. to obtain bifidobacteria fermented milk. Also, into a defatted powdered milk solution (SNF 17.4%) which was similarly subjected to plate sterilization, the pre-culture solution of *Streptococcus thermophilus* YIT 2084 was inoculated at 0.5%, followed by 24 hours of culture at 37° C. to obtain lactic acid bacteria fermented milk. The resulting bacterial solutions were mixed, into which a syrup solution, which was a mixture of reduced malt sugar syrup, polydextrose, galacto-oligosaccharide, emulsified iron, aspartame, and the like, was blended, whereby fermented milk was obtained.

It has been confirmed that *Bifidobacterium breve* YIT 4065 exerts equivalent effects to *Bifidobacterium breve* YIT 12272 in terms of the skin property-improving action by oral ingestion (i.e., TEWL, water content, the number of sulcus cutis and crista cutis, and the like), and thus the fermented milk of the present Example is expected to have the skin property-improving action of the present invention.

The invention claimed is:

1. A method for treating skin damage arising from ultraviolet radiation in a subject in need thereof, the method consisting of orally ingesting a composition consisting of, as an active ingredient, (i) a bacterium of genus *Streptococcus* and a bacterium of genus *Bifidobacterium*, (ii) fermented milk consisting of the two bacteria;
   wherein each of the bacteria are present in the composition in an amount of about $10^3$ to $10^{13}$ CFU, and are (A) the bacterium of-genus *Streptococcus* is *Streptococcus thermophilus* YIT 2021 (FERM BP-7537); and the bacterium of genus *Bifidobacterium* is *Bifidobacterium breve* YIT 12272 (FERM BP-11320);
   (B) the bacterium of genus *Streptococcus* is *Streptococcus thermophilus* YIT 2084 (FERM BP-10879); and the bacterium of genus *Bifidobacterium* is *Bifidobacterium breve* YIT 12272 (FERM BP-11320);
   (C) the bacterium of genus *Streptococcus* is *Streptococcus thermophilus* YIT 2084 (FERM BP-10879); and the bacterium of genus *Bifidobacterium* is *Bifidobacterium breve* YIT 4065 (FERM BP-8223); or
   (D) the bacterium of genus *Streptococcus* is *Streptococcus thermophilus* YIT 2021 (FERM BP-7537); and the bacterium of genus *Bifidobacterium* is *Bifidobacterium breve* YIT 4065 (FERM BP-6223).

2. The method of claim 1, further comprising orally ingesting galacto-oligosaccharide.

3. The method of claim 1, wherein the composition inhibits a reduction in water content of stratum corneum caused by ultraviolet irradiation.

4. The method of claim 1, wherein the composition promotes an increase in water content of stratum corneum.

5. The method of claim 1, wherein the bacterium of genus *Streptococcus* is *Streptococcus thermophilus* YIT 2021 (FERM BP-7537) and the bacterium of genus *Bifidobacterium* is *Bifidobacterium breve* YIT 12272 (FERM BP-11320).

6. The method of claim 1, wherein the bacterium of genus *Streptococcus* is *Streptococcus* thermophilus YIT 2084 (FERM BP-10879); and the bacterium of genus *Bifidobacterium* is *Bifidobacterium breve* YIT 12272 (FERM BP-11320).

7. The method of claim 1, wherein the bacterium of genus *Streptococcus* is *Streptococcus thermophilus* YIT 2084 (FERM BP-10879); and the bacterium of genus *Bifidobacterium* is *Bifidobacterium breve* YIT 4065 (FERM BP-6223).

8. The method of claim 1, wherein the bacterium of genus *Streptococcus* is *Streptococcus thermophilus* YIT 2021 (FERM BP-7537) and the bacterium of genus *Bifidobacterium* is *Bifidobacterium breve* YIT 4065 (FERM BP-6223).

9. The method of claim 1, wherein each of the bacteria are present in the composition in an amount of about $10^6$ to $10^{13}$ CPU.

10. The method of claim 1, wherein each of the bacteria are present in the composition in an amount of about $10^7$ to $10^{13}$ CFU.

11. The method of claim 1, wherein each of the bacteria are present in the composition in an amount of about $10^8$ to $10^{13}$ CPU.

12. The method of claim 1, wherein each of the bacteria are present in the composition in an amount of about $10^3$ to $10^8$ CFU.

13. A method for treating skin damage arising from ultraviolet radiation selected from the group consisting of inflammation, immune suppression, or DNA damage in a subject in need thereof, the method consisting of orally ingesting a composition consisting of, as an active ingredient, (i) a bacterium of genus *Streptococcus* and a bacterium of genus *Bifidobacterium*, or (ii) fermented milk comprising the two bacteria;
   wherein each of the bacteria are present in the composition in an amount of about $10^3$ to $10^{13}$ CFU, and are (A) the bacterium of-genus *Streptococcus* is *Streptococcus thermophilus* YIT 2021 (FERM BP-7537); and the bacterium of genus *Bifidobacterium* is *Bifidobacterium breve* YIT 12272 (FERM BP-11320);
   (B) the bacterium of genus *Streptococcus* is *Streptococcus thermophilus* YIT 2084 (FERM BP-10879); and the bacterium of genus *Bifidobacterium* is *Bifidobacterium breve* YIT 12272 (FERM BP-11320);
   (C) the bacterium of genus *Streptococcus* is *Streptococcus thermophilus* YIT 2034 (FERM BP-10879); and the bacterium of genus *Bifidobacterium* is *Bifidobacterium breve* YIT 4065 (FERM BP-6223); or (D) the bacterium of genus *Streptococcus* is *Streptococcus thermophilus* YIT 2021 (FERM BP-7537); and the bacterium of genus *Bifidobacterium* is *Bifidobacterium breve* YIT 4065 (FERM BP-6223).

\* \* \* \* \*

UNITED STATES PATENT AND TRADEMARK OFFICE
CERTIFICATE OF CORRECTION

PATENT NO. : 9,439,933 B2  
APPLICATION NO. : 13/805908  
DATED : September 13, 2016  
INVENTOR(S) : Norie Masuoka et al.

Page 1 of 1

It is certified that error appears in the above-identified patent and that said Letters Patent is hereby corrected as shown below:

In the Specification

Column 16, Claim 1, Line 2, "(FERM BP-8223)" should read --(FERM BP-6223)--.

Signed and Sealed this
Third Day of January, 2017

Michelle K. Lee
*Director of the United States Patent and Trademark Office*